(12) United States Patent
Iannelli

(10) Patent No.: US 8,740,971 B2
(45) Date of Patent: Jun. 3, 2014

(54) VASCULAR PROSTHESIS

(76) Inventor: Gabriele Iannelli, Naples (IT)

( * ) Notice: Subject to any disclaimer, the term of this patent is extended or adjusted under 35 U.S.C. 154(b) by 0 days.

(21) Appl. No.: 12/373,425

(22) PCT Filed: Jul. 11, 2006

(86) PCT No.: PCT/IT2006/000527
§ 371 (c)(1),
(2), (4) Date: Jan. 12, 2009

(87) PCT Pub. No.: WO2008/007397
PCT Pub. Date: Jan. 17, 2008

(65) Prior Publication Data
US 2009/0281616 A1    Nov. 12, 2009

(51) Int. Cl.
*A61F 2/06* (2013.01)
*A61F 2/82* (2013.01)

(52) U.S. Cl.
USPC ........ 623/1.35; 623/1.11; 623/1.15; 623/1.13

(58) Field of Classification Search
CPC ............................. A61F 2/07; A61F 2002/065
USPC ................ 623/1.11, 1.13, 1.15, 1.35
See application file for complete search history.

(56) References Cited

U.S. PATENT DOCUMENTS

| | | | |
|---|---|---|---|
| 5,127,919 A | | 7/1992 | Ibrahim |
| 5,810,708 A | * | 9/1998 | Woodard et al. ................ 600/16 |
| 6,099,548 A | * | 8/2000 | Taheri ........................... 606/198 |
| 6,187,033 B1 | | 2/2001 | Schmitt et al. |
| 6,723,116 B2 | * | 4/2004 | Taheri ........................... 623/1.11 |
| 2002/0156518 A1 | * | 10/2002 | Tehrani ......................... 623/1.11 |
| 2003/0109919 A1 | * | 6/2003 | Gantt et al. ................... 623/1.35 |
| 2003/0120333 A1 | | 6/2003 | Ouriel et al. |
| 2003/0199967 A1 | | 10/2003 | Hartley et al. |
| 2004/0230287 A1 | * | 11/2004 | Hartley et al. ............... 623/1.12 |
| 2005/0010277 A1 | * | 1/2005 | Chuter ......................... 623/1.13 |
| 2005/0288765 A1 | * | 12/2005 | Taheri ......................... 623/1.12 |

FOREIGN PATENT DOCUMENTS

| | | |
|---|---|---|
| WO | 99/11198 | 3/1999 |
| WO | 02/076346 | 10/2002 |

OTHER PUBLICATIONS

International Search Report for PCT/IT2006/000527, mailed Apr. 13, 2007, four pages.

* cited by examiner

*Primary Examiner* — Jason-Dennis Stewart
(74) *Attorney, Agent, or Firm* — Nixon & Vanderhye PC

(57) ABSTRACT

A vascular endoprosthesis (1) is disclosed which is capable of being arranged internally to the aortic arch (O), comprising: a tubular main body (2), to be housed in the internal lumen of the aortic arch (O); three tubular secondary bodies (3, 4, 5), originating from the main body (2) and to be housed in the right carotid artery (R), in the left carotid artery (L) and in the subclavian artery (S); and stent-type engagement means (10, 11, 13, 14, 15), intended to hold a longitudinal end portion (21, 22, 31, 41, 51) of the main and secondary bodies onto the internal wall of the respective vessel (FIG. 5).

36 Claims, 2 Drawing Sheets

VASCULAR PROSTHESIS

This application is the U.S. national phase under 35 U.S.C. 371 of International Application No. PCT/IT2006/000527, filed 11 Jul. 2006, which designated the U.S., the entire contents of which is hereby incorporated by reference.

The present invention refers to a vascular endoprosthesis, apt to exclude an aneurysmal portion of the aorta, and in particular of the aortic arch or the thoraco-abdominal aorta.

As is well-known, the aorta is the most important artery supplying blood to the organism. It originates from the heart as ascending aorta and continues at the thoracic level as aortic arch and descending aorta, subsequently extending into the abdomen where it divides, at the level of the bifurcation, into two iliac arteries. Among the arteries originating from the aorta, some are of fundamental importance: the right common carotid artery, the left common carotid artery and the left subclavian artery, all of which initiate from the aortic arch and supply blood to the cerebral region and to the upper limbs; the intercostal arteries, originating from the descending thoracic aorta to supply the spinal cord; and lastly, the visceral arteries, extending from the upper abdominal section to supply all the abdominal organs.

The aorta has an average diameter of 2 cm. and its wall is made of elastic fibres (primarily in the thoracic section) and muscular fibres (primarily in the abdominal section). Aneurysms, that is dilations of the aorta, are among the most severe pathologies affecting the aorta, in particular the thoracic and thoraco-abdominal portion.

Conventional surgery for treatment of the aneurysmal aorta-thoracic and/or thoraco-abdominal—calls for a resection of the aorta portion involved and its replacement with a prosthesis that is anastomosed between the two vascular stumps resulting from the resection. Generally, during this procedure the patient is subjected to hypothermic extracorporeal circulation.

Despite the remarkable advances made in conventional surgery over the past few years in treating aneurysms of the aortic arch and the thoraco-abdominal aorta, major problems that decisively condition surgical results remain unresolved, as conventional surgery is still burdened by high mortality and morbidity, with a particularly high risk of paraplegia, cerebral ischemia, respiratory and/or renal insufficiency, etc. The major problems conditioning surgical results ensue from the lengthy times required for the "aortic cross-clamping" to suture the prosthesis in situ, and from the use of extracorporeal circulation systems, the latter intended to protect such particularly sensitive organs as the central nervous system, the cardiovascular system, renal function, etc.

The advent of endovascular surgery in the surgical panorama of the last decade has certainly modified and improved surgical results for treatment of the aneurysmal pathology, especially of the descending thoracic aorta, significantly decreasing the incidence of such serious complications as paraplegia. The endovascular approach requires no resection of the aortic portion involved by the aneurysm, but simply the insertion of an endoprosthesis that reproduces the correct vascular diameter, thereby excluding the aneurysm and re-establishing a correct blood flow. Said significant improvement is certainly attributable to the elimination of aortic cross-clamping, the need for extracorporeal circulation and of other organ protection systems requiring lengthy and extensive use of anesthesia.

Regrettably, endovascular surgery, certainly valid for the descending thoracic aorta, has found no effective application for the aortic arch and for the thoraco-abdominal aorta, where attempts have proved wholly unsatisfactory and are limited exclusively to a "hybrid" treatment combining a conventional surgical approach and an endovascular approach.

Thus the technical problem presented and solved by the present invention is to provide a vascular prosthesis capable of overcoming the drawbacks mentioned hereto with reference to the known procedure.

The problem is solved by a vascular endoprosthesis as per claim 1.

Preferred features of the present invention are provided for in the dependent claims thereof.

The present invention provides several relevant advantages. The main advantage lies in that the prosthesis of the invention allows for a drastic reduction of the time required for the in situ anastomoses of the prosthesis itself and obviates the need for extracorporeal circulation and organ protection systems. Hence, it significantly reduces surgical and anaesthesia times, leading to optimal treatment of the aneurysm pathology of the aortic arch and of the thoraco-abdominal aorta.

Other advantages, features and operation modes of the present invention will be elucidated in the following detailed description of some of the embodiments thereof, given by way of example and not wholly exhaustive. Reference will be made to the annexed drawings, wherein.

Figure 1:
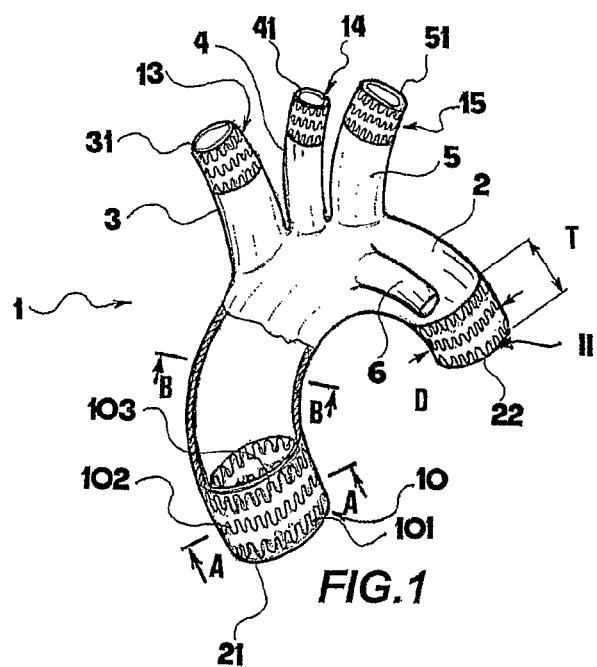
FIG. 1 shows a schematic front perspective view of an embodiment of the vascular endoprosthesis according to the present invention.
Figure 4:
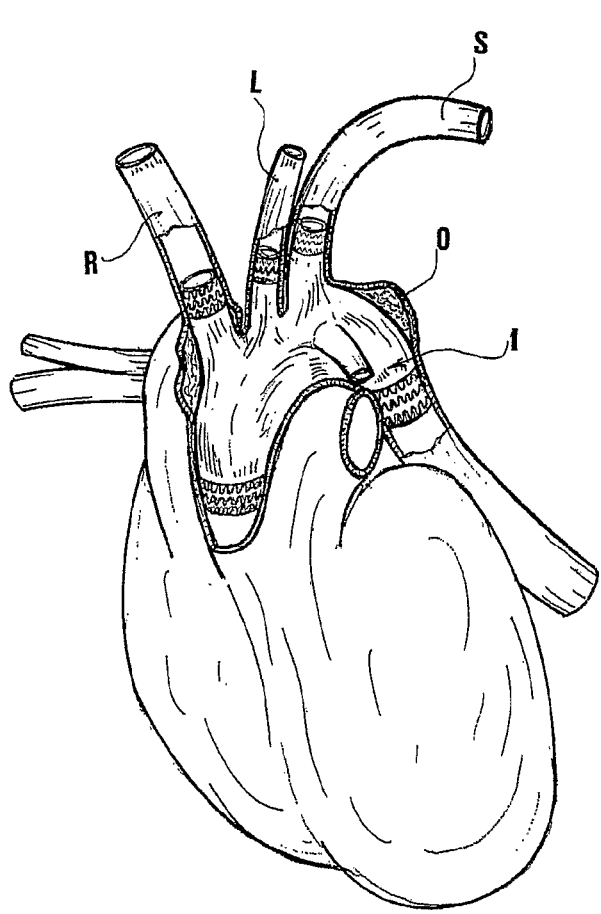
Figure 5:
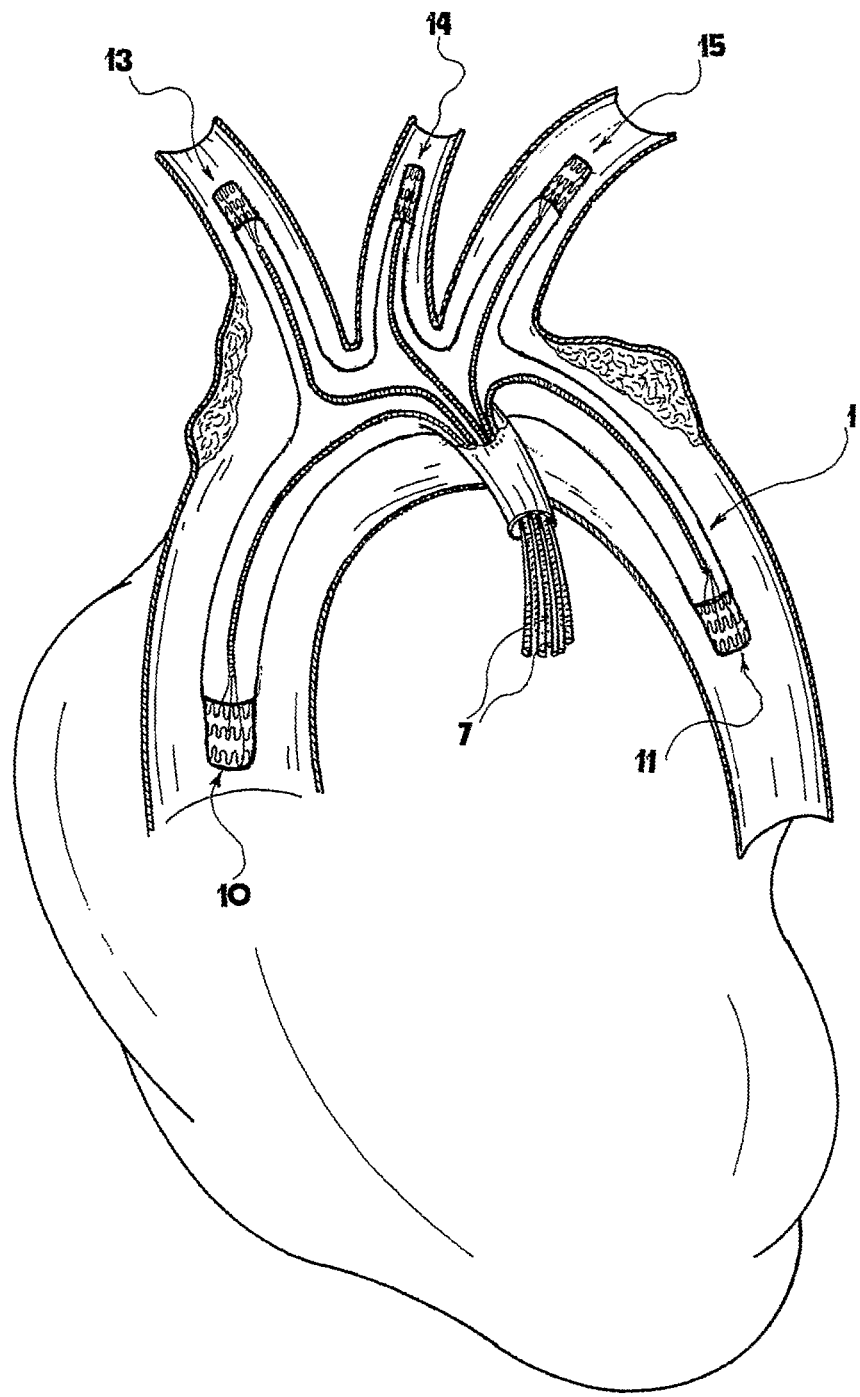

FIG. 4 shows a perspective view of the endoprosthesis of FIG. 1 implanted in correspondence of a section of the aortic arch; and FIG. 5 shows a partially sectional perspective view of the endoprosthesis of FIG. 1 during its insertion in correspondence with the section of the related aortic arch, before the opening of the ends equipped with metal supports and with part of the prosthesis still external to the aneurysm.

Initially referring to FIG. 1, a vascular endoprosthesis according to an embodiment of the invention is generally denoted by 1. In the present example, the endoprosthesis 1 is conceived to be implanted in correspondence with the aortic arch, and FIG. 4 shows the endoprosthesis 1 in situ.

The endoprosthesis 1 comprises a substantially tubular main body 2 intended to be lodged in the internal lumen of the aortic arch, denoted by O in FIG. 4.

Three secondary bodies branch off from main body 2. These are also tubular and marked 3, 4 and 5, respectively, each of which to be inserted into the internal lumen of a blood vessel originating from the aortic arch. In particular, the first secondary body 3 is intended to be inserted into the right common carotid artery, denoted by R in FIG. 4, the second secondary body 4 into the left common carotid artery, denoted by L, and the third secondary body 5 into the left subclavian artery, denoted by S.

Figure 3:
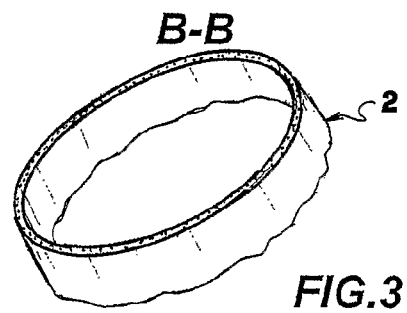
FIG. 3 shows another cross section of the prosthesis of FIG. 1, taken along line B-B of the latter Figure.

Referring also to the section of FIG. 3, both the main body 2 and the secondary bodies 3-5 are made of impermeable biocompatible material. Ideally, this material should be elastically deformable and furrowed, (corrugated) e.g. Dacron.

In correspondence with each of the two longitudinal end portions 21 and 22 of the main body 2 are respective engagement means, denoted by 10 and 11, respectively, to secure end portions 21 and 22 to the internal wall of the corresponding section of the aortic arch. Engagement means 10, 11 are shown in greater detail in FIG. 2.

In this example, fixing means 10 and 11 are based on self-expandable elastic elements set onto the internal walls of the blood vessels, in an expanded configuration. Specifically, each of means 10, 11 consists of a shaped annular weft made of (biocompatible) elastically deformable material, externally surrounding and being supported by the respective end portions 21, 22 of the main body 2, the latter preferably made of the same biocompatible elastically deformable material. Preferably, in correspondence with said ends 21, 22, the material should not be furrowed. (corrugated)

In the present example said weft is formed by three independent metallic annular elements, denoted by 101, 102 and 103, respectively, for the means 10, each having a substantially sinusoidal or loop-shaped profile. These annular elements are circumferentially arranged onto the main body 2 and longitudinally spaced in correspondence with the respective end portion 21, 22. Preferably, and analogously to stent-type securing systems already used in existing endoprostheses, the means 10, 11 are made of a shape retentive material, typically thermally preformed Nitinol or an alloy thereof.

The annular elements of 101-103 type are secured on the end portions 21, 22 of the main body 2, e.g. by suture.

Figure 2A:
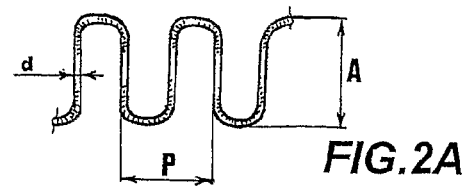
FIG. 2A illustrates some geometric parameters of a component of the prosthesis of FIG. 1.
Figure 2:
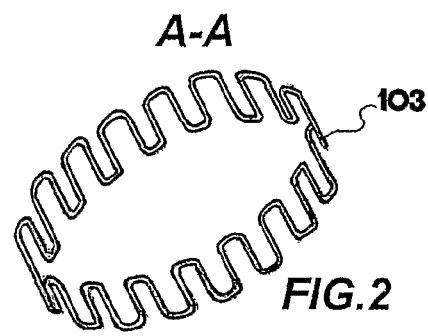
FIG. 2 shows a cross section of the prosthesis of FIG. 1 taken along line A-A of the latter Figure.

As shown in FIG. 2A, preferably each annular element 101-103 has a pitch P equal to about 10 mm, a loop width A equal to about 8 mm and a wire diameter d comprised in a range of about 0.1-1.0 mm.

Moreover, the engagement means 10, 11 each preferably involve a distal section T of the main body 2, of an approximate length comprised between 2-3 cm and of diameter, or gauge, D ranging between 26-46 mm.

Each of the secondary bodies 3-5 further comprises, in correspondence with a respective distal end 31, 41, 51 thereof, respective engagement means 13, 14, 15, having an overall configuration analogous to that of the above-described means 10, 11.

Of course, the specific dimensions and extension of engagement means 13-15 of the secondary bodies 3-5 will be adapted to the configuration of the respective blood vessel of insertion. In particular, for the secondary bodies 3-5 the pitch P could equal about 2 mm, a wire diameter d equal to about 0.4 mm and a distal section, concerned by means 13-15, of length T equal to about 20 mm and diameter D equal to about 8-14 mm.

Preferably, in correspondence with engagement means 10, 11 and 13-15 the diameter of the respective main 2 and secondary 3-5 bodies (and therefore that of the related annular elements) is oversized with respect to that of the respective blood vessel in a percentage equal to about 10-15% of the diameter of the vessel itself, and this in order to allow for improved securing in situ of the endoprosthesis 1.

The provision of the engagement means only distally to each of the bodies 2-5 allows for improved adaptation to the anatomical site of the endoprosthesis 1 as a whole, leaving the central part of the main body 2 and of the secondary bodies 3-5 free for adaptation.

The engagement means 10, 11 and 13-15 assume an initial configuration of minimal encumbrance, shown in FIG. 5, in which they are compressed or folded to allow for insertion of the respective body 2-5 into the related blood vessel, and a second unfolded or extended configuration, shown in FIG. 4, in which they engage the wall of the blood vessel itself, securing the endoprosthesis 1 in situ.

The engagement means 10, 11 and 13-15 can be remotely controlled (maneuvered) to allow transition from the first to the second configuration mentioned hereto. For this purpose, the endoprosthesis 1 comprises a fourth tubular body 6 forming a maneuvering channel and arranged in a position substantially centered with respect to the main body 2 and, with the endoprosthesis in situ, below the secondary bodies 3-5. In the present example, maneuvering channel 6 has a diameter of about 10 mm. This maneuvering channel 6 can house one or more maneuvering elements 7 accessible from the outside, and in particular, as shown in the example in FIG. 5, several maneuvering wires to unfold each of the engagement means 10, 11 and 13-15.

Upon implant of the endoprosthesis 1, the procedure described below is carried out, with reference to the example applicable to the aortic arch and the related epiaortic vessels.

First, the aortic segment to be treated is exposed, using a conventional surgical approach of codified cuts, such as median sternotomy or bilateral thoracotomy for the aortic arch or thoracophrenolaparotomy for the thoraco-abdominal aorta.

The portions of blood vessels at which the engagement means 10, 11 and 13-15 are to be positioned are non-aneurysmal sections adjacent to the aneurysmal portions. At each of the "healthy" portions, the physician, usually a vascular surgeon, performs a "purse string", a technique familiar to experts in the field and consisting in a pair of side-by-side stitches intended to constrict the section of vessel involved when pulled.

The example presented is of five "purse string" performed on healthy arterial wall, i.e. at the level of the ascending aorta (in correspondence with the end portion of the proximal end 21 of the endoprosthesis 1), at the level of the descending thoracic aorta (in correspondence with the final position of the distal end 22) and at the level of the epiaortic vessels (in correspondence with the final position of the collateral ends 31, 41 and 51 relating to the right common carotid artery R, the left common carotid artery L and the left subclavian artery S, respectively).

After partial heparinization and using the well-known Seldinger technique, five ends of the endoprosthesis 1 are inserted, containing the rapid-expansion engagement means 10, 11 and 13-15, which are held in place by the five previously performed purse strings and held in compressed configuration by the maneuvering wires 7.

Upon positioning the endoprosthesis 1—which is not yet operative—as mentioned above, the five ends 21, 22, 31, 41 and 51 are unfolded, i.e. brought from the compressed configuration to the extended one, in the following sequence:

I. left subclavian artery-related end 51,
II. left carotid artery-related end 41,
III. right carotid artery-related end 31,
IV. proximal aorta-related end 21,
V. distal aorta-related end 22.

With the unfolding of the engagement means 10, 11 and 13-15 anastomeses are executed with the aortic arch O and one of the above mentioned epiaortic vessels R, L and S. Note that the engagement means 10, 11 and 13-15 allows for the performance of the anastomoses not though a vascular suture, but rather through an endovascular-type release system; thus we may in effect define it as "endoanastomosis".

The time of execution for the five anastomoses is envisaged to be less than two minutes, certainly brief enough as not to create ischemic problems to the brain.

Of course, each of the maneuvering wires 7 of the channel 6 could be indicated by a suitable identifying element, e.g. an alphanumeric character, of the respective maneuvered engagement means 10, 11 and 13-15, visible from the outside.

The above-indicated sequence (I)-(V) allows for effective purging of air from the epiaortic trunks, preventing the risk of embolizing the brain.

It should be noted that the proposed configuration, in which the five ends of the maneuvering wires 7 issue from the sole collateral branch of the prosthesis 1 not equipped with stents, i.e. from the maneuvering channel 6, also facilitates control of the endoprosthesis 1 itself and the purging of air to the outside.

Once the endoprosthesis 1 in place is operating, and after checking that the aneurysmal sac is no longer supplied as it is excluded from the circulation, the aneurysm is opened up.

Note that in the present example, since the collateral branch 3 is inserted directly into the right common carotid artery R, and not into the brachiocephalic trunk (in order to simplify and unify the gauges of the collateral branches) a surgical revascularization of the right subclavian artery should be provided for; such a revascularization can be carried out at leisure at the conclusion of the procedure by using the collateral branch 6.

This particular endoprosthesis may also be used for replacement of the thoraco-abdominal aorta, in such case using four secondary bodies to be inserted into the celiac tripod, the superior mesenteric artery, the right renal artery and the left renal artery.

Moreover, in case of need the prosthesis described hereto may also be used in conventional surgery, by resecting the proximal or distal end equipped with a stent (or by removing the endoanastomosis site) and suturing it to the residual (ascending and/or descending) aortic stump, for highly extensive pathologies, such as acute type A dissections or Marfan syndrome.

Furthermore, it will be appreciated that this invention means that a single item can fulfill the needs for treatment of the aortic arch and of the thoraco-abdominal aorta, thus simplifying its implementation and marketing.

Thanks to its simplicity and speed of use, the invention also offers the potential of expanding the range of operators who can carry out vascular prosthetic fitting surgery, increasing then number of potential beneficiaries to include vascular surgery centers currently not able to provide these types of treatment.

It should be apparent by now that the above-described vascular prosthesis would drastically reduce surgical times from the current approximate 120-180 min to the 4-5 min required for preparation of the entire technique.

The invention further refers to a method of treating vascular pathologies that, in its broadest definition envisages:
  providing an endoprosthesis as defined above, and comprising in particular a substantially tubular main body capable of being introduced into the internal lumen of a main blood vessel and at least one secondary body, also basically tubular and originating from said main body, capable of being introduced into the internal lumen of a secondary blood vessel branching off the main vessel;
  inserting said endoprosthesis into the main and secondary blood vessels; and
  setting and securing the endoprosthesis in position.

The present invention has hereto been described with reference to preferred embodiments thereof. It is understood that there might be other embodiments referable to the same inventive principle, all falling within the protective scope of the claims hereinafter.

The invention claimed is:

1. A vascular endoprosthesis capable of being set internally to a blood vessel, in particular a portion of aorta, comprising:
  a substantially tubular main body, to be housed in the internal lumen of a main blood vessel;
  at least one secondary body, also substantially tubular, and originating from and fixed to said main body, to be housed in the internal lumen of a blood vessel branching off the main vessel;
  engagement means, associated with and fixed to each of said main body and secondary body and arranged in correspondence with at least one respective longitudinal end portion of each, apt to hold said end portions onto the internal wall of the respective blood vessel; and
  a maneuvering channel originating from said main body and, wherein the maneuvering channel is configured for remotely controlling the configuration of said engagement means;
wherein said vascular endoprosthesis is pre-assembled prior to being implanted in situ.

2. The endoprosthesis according to claim 1, wherein said engagement means are apt to assume a first configuration of minimal encumbrance, allowing for insertion of the respective main or secondary body into the related blood vessel, and a second unfolded configuration, engaging the wall of the blood vessel, securing in position the respective longitudinal end of said main or secondary body.

3. The endoprosthesis according to claim 2, wherein said engagement means are apt to be circumferentially compressed to assume said configuration of minimal encumbrance.

4. The endoprosthesis according to claim 1, wherein said engagement means are self-expandable.

5. The endoprosthesis according to claim 1, wherein said engagement means are arranged onto the external wall of the respective main or secondary body.

6. The endoprosthesis according to claim 1, wherein said engagement means comprise one or more elastically deformable elements.

7. The endoprosthesis according to claim 6, wherein said or each of said elastically deformable element or elements comprises an annular element circumferentially arranged onto the respective main or secondary body.

8. The endoprosthesis according to claim 6, wherein said or each of said elastically deformable elements comprises a loop-shaped element.

9. The endoprosthesis according to claim 6, wherein said engagement means comprise several elastically deformable elements arranged longitudinally side-by-side along the respective main or secondary body.

10. The endoprosthesis according to claim 1, wherein said engagement means comprise one or more stent-type elements.

11. The endoprosthesis according to claim 1, wherein said engagement means comprise one or more shape memory-type elements.

12. The endoprosthesis claim 1, comprising maneuvering means that can be operated from the outside for remote control of the configuration of said engagement means.

13. The endoprosthesis according to claim 12, wherein said maneuvering means comprise one or more maneuvering wires.

14. The endoprosthesis according to claim 12, wherein said maneuvering means bear identifying elements of the respective engagement means.

15. The endoprosthesis according to claim 1, wherein said main body is apt to be housed in a portion of aorta.

16. The endoprosthesis according to claim 15, wherein said main body is apt to be housed in the thoraco-abdominal aorta.

17. The endoprosthesis according to claim 15, wherein said main body is apt to be housed in the aortic arch.

18. The endoprosthesis according to claim 17, comprising a secondary body apt to be housed in the right carotid artery.

19. The endoprosthesis according to claim 17, comprising a secondary body apt to be housed in the left carotid artery.

20. The endoprosthesis according to claim 17, comprising a secondary body apt to be housed in the left subclavian artery.

21. The endoprosthesis according to claim 1, wherein said main body and/or said secondary body or bodies are made of an elastically deformable material.

22. The endoprosthesis according to claim 1, wherein said main body and/or said secondary body or bodies are at least partially made of a furrowed (corrugated) material.

23. The endoprosthesis according to claim 1, wherein, in correspondence of said engagement means, the diameter of the respective main and/or secondary body is oversized with respect to that of the respective blood vessel of insertion.

24. The endoprosthesis according to claim 23, wherein said oversizing is comprised in a range of about 10-15%.

25. A method of treating vascular pathologies, comprising the following steps:
(a) providing an endoprosthesis of claim 1, comprising a substantially tubular main body to be housed in the internal lumen of a main blood vessel and at least one secondary body, also substantially tubular and originating from said main body, apt to be housed in the internal lumen of a secondary blood vessel branching off the main vessel;
(b) inserting said endoprosthesis into said main and secondary blood vessels; and
(c) securing said endoprosthesis in position.

26. The method according to claim 25, which is a method of treating aneurysmal blood vessels.

27. The method according to claim 25, wherein said main blood vessel is the aorta.

28. The method according to claim 27, wherein said step (b) provides for the insertion of the main body of the endoprosthesis into the aortic arch.

29. The method according to claim 28, wherein said step (b) provides for the insertion of the secondary body or bodies of the endoprosthesis into one or more blood vessels selected from a group comprising the right carotid artery, left carotid artery and left subclavian artery.

30. The method according to claim 29, wherein said step (c) provides for the clamping of the endoprosthesis in situ by activating related holding means according to the sequence: (I) left subclavian artery; (II) left carotid artery; (III) right carotid artery; (IV) proximal aorta; (V) distal aorta.

31. The method according to claim 27, wherein said step (b) provides for the insertion of the main body of the endoprosthesis into the thoraco-abdominal aorta.

32. The method according to claim 25, wherein said step (b) provides for the temporary setting and securing in situ of the endoprosthesis by temporary restriction of the internal vascular lumen of healthy vascular portions.

33. The method according to claim 32, wherein said temporary restriction of the internal lumen of healthy vascular portions is obtained by performing "purse string" in correspondence with said portions.

34. The method according to claim 25, providing for removal of a vascular portion external to the endoprosthesis, performed in a surgical procedure temporally separate from that of insertion of the endoprosthesis itself.

35. The method according to claim 25, wherein said step (a) provides for the use of an endoprosthesis capable of being set internally to a blood vessel, in particular a portion of aorta, comprising:
a substantially tubular main body, to be housed in the internal lumen of a main blood vessel;
at least one secondary body, also substantially tubular, and originating from and fixed to said main body, to be housed in the internal lumen of a blood vessel branching off the main vessel;
engagement means, associated with and fixed to each of said main body and secondary body and arranged in correspondence with at least one respective longitudinal end portion of each, apt to hold said end portions onto the internal wall of the respective blood vessel; and
a maneuvering channel originating from said main body and, wherein the maneuvering channel is configured for remotely controlling the configuration of said engagement means;
wherein said vascular endoprosthesis is pre-assembled prior to being implanted in situ.

36. A vascular endoprosthesis capable of being set internally to a blood vessel, in particular a portion of aorta, comprising:
a substantially tubular main body, to be housed in the internal lumen of a main blood vessel;
a plurality of secondary bodies, which are substantially tubular and fixed to said main body, to be housed in the internal lumen of a blood vessel branching off the main vessel;
engagement means, which is fixed to each of said main body and secondary body, arranged in correspondence with at least one respective longitudinal end portion of each, apt to hold said end portions onto the internal wall of the respective blood vessel; and
a maneuvering channel originating from said main body and, wherein the maneuvering channel is configured for remotely controlling the configuration of said engagement means;
wherein said main body and said secondary bodies are made as a single body, and said vascular endoprosthesis is pre-assembled prior to being implanted in situ.

* * * * *